US012569286B2

(12) United States Patent
Sancho et al.

(10) Patent No.: US 12,569,286 B2
(45) Date of Patent: Mar. 10, 2026

(54) ACCURACY OF ABLATION MODEL THROUGH SYNCHRONIZATION

(71) Applicant: Medlumics S.L., Madrid (ES)

(72) Inventors: Juan Sancho, Madrid (ES); David Herranz, Alpedrete (ES); Christophe Bailleul, Paris (FR); James Greene, Shelfield Green (GB)

(73) Assignee: Medlumics S.L., Madrid (ES)

( * ) Notice: Subject to any disclaimer, the term of this patent is extended or adjusted under 35 U.S.C. 154(b) by 249 days.

(21) Appl. No.: 18/205,962

(22) Filed: Jun. 5, 2023

(65) Prior Publication Data

US 2023/0397942 A1 Dec. 14, 2023

(30) Foreign Application Priority Data

Jun. 9, 2022 (EP) .................................... 22382553

(51) Int. Cl.
  *A61B 18/00* (2006.01)
  *G16H 40/63* (2018.01)
  (Continued)

(52) U.S. Cl.
  CPC ............. *A61B 18/00* (2013.01); *G16H 40/63* (2018.01); *A61B 2017/00057* (2013.01);
  (Continued)

(58) Field of Classification Search
  CPC ......... A61B 18/00; A61B 18/02; A61B 18/08; A61B 18/14; A61B 18/1482;
  (Continued)

(56) References Cited

U.S. PATENT DOCUMENTS

2011/0028967 A1 2/2011 Rollins et al.
2017/0354357 A1 12/2017 Laughner et al.
(Continued)

OTHER PUBLICATIONS

González-Suárez et al., "Relation Between Denaturation Time Measured by Optical Coherence Reflectometry and Thermal Lesion Depth During Radiofrequency Cardiac Ablation: Feasibility Numerical Study", Laser in Surgery and Medicine (2018), pp. 222-229, 2017 Wiley Periodicals, Inc.
(Continued)

*Primary Examiner* — George Manuel
(74) *Attorney, Agent, or Firm* — Sterne, Kessler, Goldstein & Fox P.L.L.C.

(57) ABSTRACT

Disclosed herein are system, method, and computer-readable medium aspects for improving the accuracy of an ablation model through synchronization. An aspect operates by activating a catheter energy source, acquiring a catheter energy signal from the catheter energy source, assigning an activation time stamp and deactivation time stamp to the catheter energy signal, and determining a time of ablation based on a time period between the activation time stamp and deactivation time stamp. The aspect continues to operate by acquiring an optical measurement signal from a catheter optical port, assigning an input time stamp and switching time stamp to the optical measurement signal, and processing the optical measurement signal in order to acquire a denaturation result. The aspect concludes by synchronizing the time of ablation and the denaturation result using the time stamps in order to generate a synchronized model and generating an estimated lesion depth from the synchronized model.

33 Claims, 7 Drawing Sheets

300

(51) Int. Cl.
*A61B 17/00* (2006.01)
*A61B 90/00* (2016.01)

(52) U.S. Cl.
CPC .............. *A61B 2017/00199* (2013.01); *A61B 2017/00292* (2013.01); *A61B 2018/00577* (2013.01); *A61B 2018/00886* (2013.01); *A61B 2090/3614* (2016.02)

(58) Field of Classification Search
CPC ............... A61B 18/1492; A61B 18/24; A61B 2017/00057; A61B 2017/00199; A61B 2017/00292; A61B 2018/00029; A61B 2018/00035; A61B 2018/00166; A61B 2018/00172; A61B 2018/00577; A61B 2018/00613; A61B 2018/00886; A61B 2018/00982; A61B 2018/00994; A61B 2018/167; A61B 2034/104; A61B 2090/306; A61B 2090/309; A61B 2090/3614; A61B 2090/3735; A61B 2090/3966; A61B 2218/002; A61B 2218/007; A61B 2562/0233; A61B 5/0036; A61B 5/0066; A61B 5/6852; A61B 5/7285; G16H 20/40; G16H 30/40; G16H 40/63; G16H 40/67; G16H 50/20; G16H 50/50
See application file for complete search history.

(56) References Cited

U.S. PATENT DOCUMENTS

2019/0015012 A1*  1/2019  Raudins ................. A61B 34/20
2021/0212569 A1    7/2021  Sancho Durá et al.

OTHER PUBLICATIONS

Flynn, Joseph, "The 'Temperature Integral'—Its Use and Abuse," Thermochimica Acta 300 (1997) 83-92.

Herranz, D. et al., "Novel Catheter Enabling Simultaneous Radiofrequency Ablation and Optical Coherence Reflectometry," Biomedical Optics Express, Aug. 7, 2015, 7;6(9): 3268-75.

Liu, Feng et al., "The Role of Protein Loss and Denaturation in Determining Outcomes of Heating, Cryotherapy, and Irreversible Electroporation on Cardiomyocytes," Journal of Biomedical Engineering, Jun. 2018, vol. 140, 061007-1-9.

* cited by examiner

Figure 5:
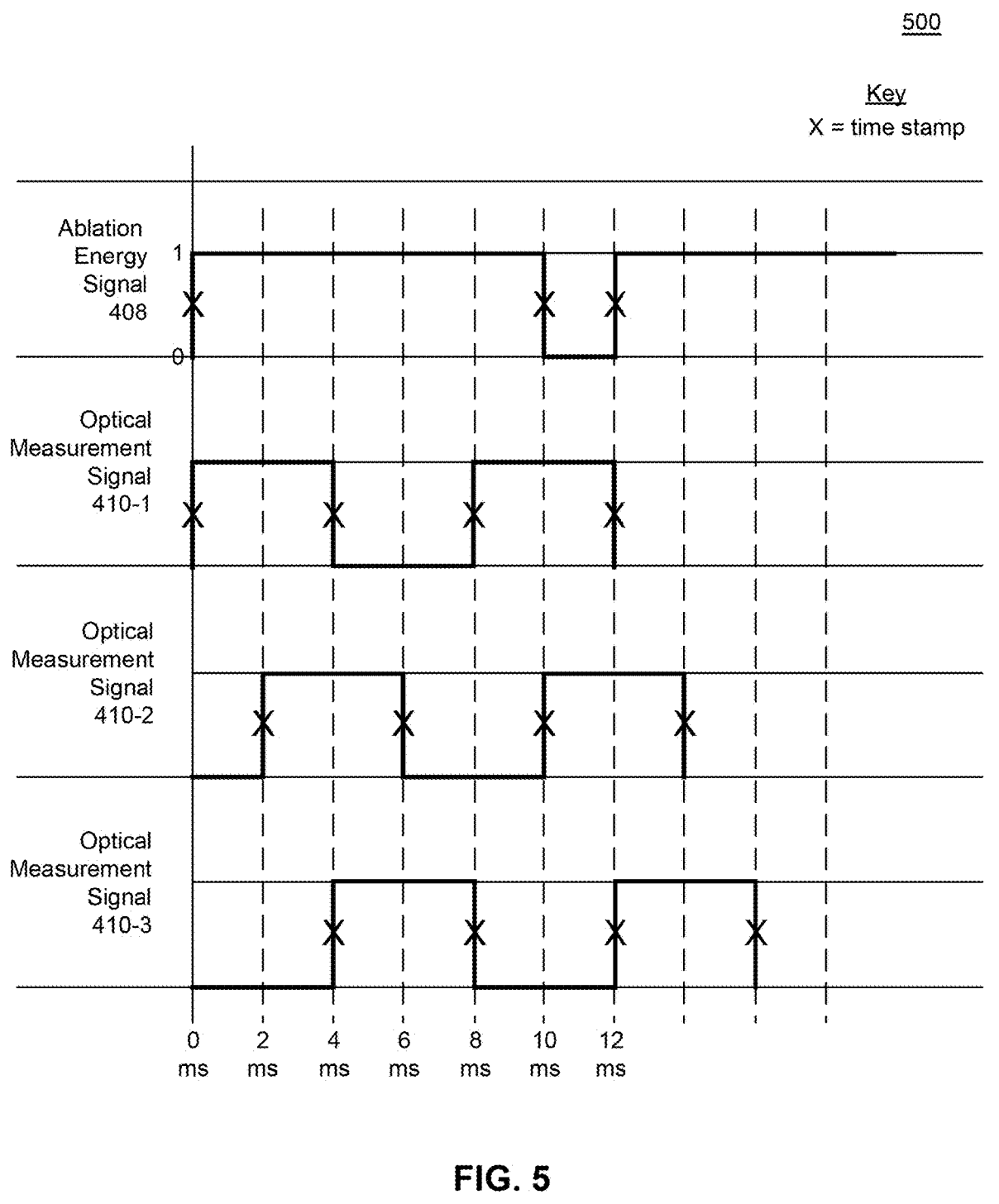

500

Key
X = time stamp

Ablation Energy Signal 408

Optical Measurement Signal 410-1

Optical Measurement Signal 410-2

Optical Measurement Signal 410-3

Computer System 700

Communication Infrastructure 706

Processor 704

Main Memory 708

User Input/Output Interface(s) 702

User Input/Output Device(s) 716

Secondary Memory 710

Hard Disk Drive 712

Removable Storage Drive 714

Removable Storage Unit 718

Interface 720

Removable Storage Unit 722

Communications Interface 724

Remote device(s), network(s), entity(ies) 728

Communications Path 726

ACCURACY OF ABLATION MODEL THROUGH SYNCHRONIZATION

CROSS-REFERENCE TO RELATED APPLICATIONS

This application claims priority to EP Appl. No. 22382553.0 filed on Jun. 9, 2022, the disclosure of which is incorporated by reference herein in its entirety.

BACKGROUND

Technical Field

Aspects of the present disclosure relate to components, systems, and methods for using devices for ablating tissue, optical signal analysis, synchronizing signals using time stamps, assessing ablation lesions, and estimating lesion depths.

Background

Ablation is a medical technique for producing tissue necrosis. It is used to help treat different pathologies including cancer, Barret's esophagus, or cardiac arrhythmias, among others. Various energy sources may be utilized for ablation. For example, in radiofrequency (RF) ablation, an external electrode is placed on a patient's body, and an alternating potential is applied to the tip of a catheter that is placed in contact with the tissue to be treated within the patient's body. The application of alternating current with an oscillating frequency above several hundreds of kHz avoids the stimulation of excitable tissue while delivering heat by means of the Joule's effect. The increase in tissue temperature produces denaturation and changes in tissue fiber anistrophy of the biological molecules, including proteins such as collagen, myosin, or elastin.

SUMMARY

In aspects presented herein, processing devices may synchronize signals from catheter systems and optical systems using time stamps in order to improve the accuracy of an ablation model from which an estimated lesion depth can be generated.

In an aspect, an example method comprises activating a catheter energy source, acquiring a catheter energy signal from the catheter energy source, assigning an activation time stamp and deactivation time stamp to the catheter energy signal, and determining a time of ablation based on a time period between the activation time stamp and deactivation time stamp. The method then comprises acquiring an optical measurement signal from a catheter optical port, assigning an input time stamp and switching time stamp to the optical measurement signal, and processing the optical measurement signal in order to acquire a denaturation result. The method further comprises synchronizing the time of ablation and the denaturation result using the time stamps in order to generate a synchronized model and generating an estimated lesion depth from the synchronized model.

In another aspect, an example system is described. The system comprises a catheter energy source, a catheter coupled to the catheter energy source, a catheter optical port, and a computing device coupled to the catheter energy source and the catheter. The computing device comprises a processor and a memory. The memory contains instructions that when executed, the processor causes the computing device to activate the catheter energy source, acquire a catheter energy signal from the catheter energy source, assign an activation time stamp and deactivation time stamp to the catheter energy signal, and determine a time of ablation based on a time period between the activation time stamp and deactivation time stamp. The processor then causes the computing device to acquire an optical measurement signal from the catheter optical port, assign an input time stamp and switching time stamp to the optical measurement signal, and process the optical measurement signal in order to acquire a denaturation result. The processor further causes the computing device to synchronize the time of ablation and the denaturation result using the time stamps in order to generate a synchronized model and to generate an estimated lesion depth from the synchronized model.

In yet another aspect, an example non-transitory computer-readable medium has instructions stored on it that, when executed by at least one computing device, cause the at least one computing device to perform operations. The operations comprise activating a catheter energy source, acquiring a catheter energy signal from the catheter energy source, assigning an activation time stamp and deactivation time stamp to the catheter energy signal, and determining a time of ablation based on a time period between the activation time stamp and deactivation time stamp. The operations then comprise acquiring an optical measurement signal from a catheter optical port, assigning an input time stamp and switching time stamp to the optical measurement signal, and processing the optical measurement signal in order to acquire a denaturation result. The operations further comprise synchronizing the time of ablation and the denaturation result using the time stamps in order to generate a synchronized model and generating an estimated lesion depth from the synchronized model.

Further features and advantages, as well as the structure and operation of various aspects, are described in detail below with reference to the accompanying drawings. It is noted that the specific aspects described herein are not intended to be limiting. Such aspects are presented herein for illustrative purposes only. Additional aspects will be apparent to persons skilled in the relevant art(s) based on the teachings contained herein.

BRIEF DESCRIPTION OF THE DRAWINGS

The accompanying drawings, which are incorporated herein and form a part of the specification, illustrate aspects of the present disclosure and, together with the description, further serve to explain the principles of the disclosure and to enable a person skilled in the pertinent art to make and use the disclosure.

FIG. 5 is a timing diagram including time stamps used for improving the accuracy of an ablation model through synchronization, according to some aspects of the present disclosure.

In the drawings, like reference numbers generally indicate identical or similar elements. Aspects of the present disclosure will be described with reference to the accompanying drawings.

DETAILED DESCRIPTION

Figure 1:
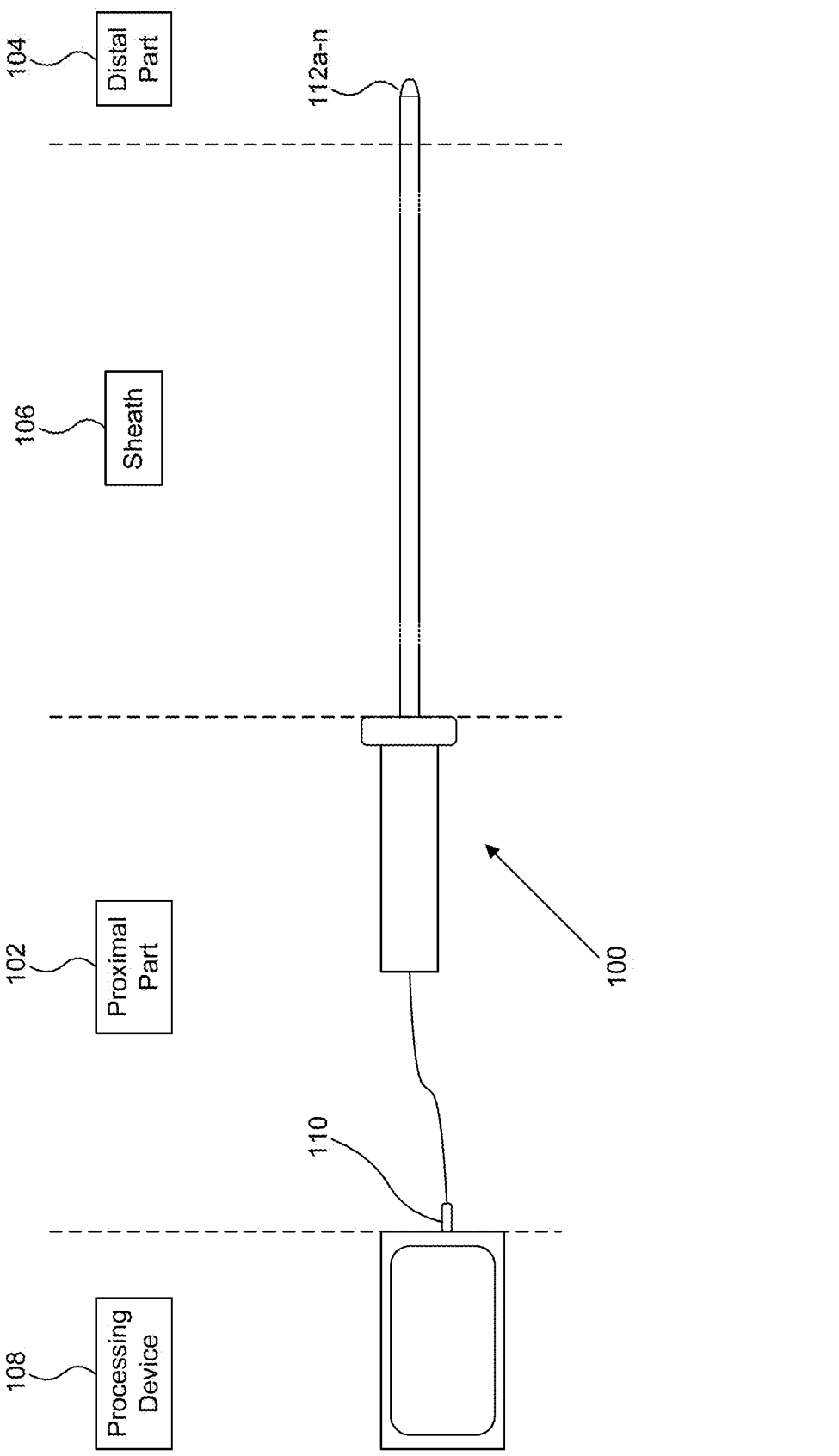
FIG. 1 illustrates an example diagram of a catheter, according to embodiments of the present disclosure.

Provided herein are system, apparatus, device, method and/or computer-readable medium aspects, and/or combinations and sub-combinations thereof for improving the accuracy of an ablation model through synchronization.

Denaturation of biological molecules of tissue creates a lesion on the tissue. Assessing characteristics of the lesion is important to producing tissue necrosis sufficient to treat different pathologies without damaging healthy tissue. The lesion can be assessed using optical ports located at the tip of the catheter and various optical data processors. Because of asynchronous acquisition and processing of various signals, it may be difficult to understand ablation effects in tissue and to avoid damaging healthy tissue using current systems and methods. Current systems and method for generating ablation models and estimating lesion depth do not provide the accuracy needed to prevent improper denaturation of biological molecules due to a synchronicity of signal acquisition and processing. Improper denaturation occurs where a lesion is created on a tissue in order to treat different pathologies but where healthy tissue is damaged due to an over-ablation of the tissue, or where the tissue is not sufficiently ablated.

In a system that does not use a time stamping approach to generate an estimated lesion depth from a synchronized model, an ablation signal and a signal relating to optical measurement of a tissue may not correspond to one another. Thus, a user may view an estimated lesion depth and believe it accurately reflects a correspondence between an amount of energy applied to a tissue and the extent of denaturation of the tissue. Based on this information, the user may improperly continue or improperly stop applying energy to the tissue. In actuality, the extent of denaturation of the tissue may be more or less than expected, resulting in damaged healthy tissue or undamaged unhealthy tissue.

Aspects herein solve these technological problems using an innovative time stamping approach that generates an estimated lesion depth from a synchronized model. An ablation catheter containing a multi-port optical component may be used to apply energy, from an energy source, to a tissue and to transmit optical measurement data from different tissue sites, through the catheter, to a console for processing. In such an aspect, the energy source may either be activated or deactivated, and only one optical port may actively provide optical measurement data at a given time. A clock in the console for processing may be used to assign time stamps to data items in order to track the status of the energy source and the data from the optical ports. Once data items have been time stamped, the console can generate an estimated lesion depth that reflects an accurate timing relationship between energy applied to the tissue and the optical measurement data from the different tissue sites.

According to aspects of the invention, a processor may assign an activation time stamp and a deactivation time stamp to a catheter energy signal (that is, the ablation signal) in accordance with the activation and deactivation of a catheter energy source. The processor may also assign an input time stamp and a switching time stamp to an optical measurement signal in accordance with the acquisition of the optical measurement signal from a catheter optical port of a catheter. The processor may determine a time of ablation and denaturation result using the signals, synchronize the time of ablation and denaturation result using the time stamps in order to generate a synchronized model, and generate an estimated lesion depth from the synchronized model. Because the estimated lesion depth is generated from the synchronized model, there is an accurate relation between when energy is applied to a tissue and when denaturation occurs in the tissue.

Aspects herein provide various benefits. For example, the time stamping approach provides an accurate estimated lesion depth to a user that reflects when the user applies energy to a tissue and when denaturation occurs in the tissue. In other words, while a user is ablating a tissue and producing tissue necrosis to treat different pathologies, the user can accurately assess characteristics of the ablation lesion to ensure that pathologies are treated and healthy tissue is protected. Therefore, the time stamping approach solves the above technological problem by improving the accuracy of an ablation model through synchronization in order to allow for the treatment of different pathologies without damaging healthy tissue.

It is noted that although this application may refer specifically to cardiac ablation, the aspects described herein may target other pathologies as well, along with additional energy sources for ablation, including but not limited to cryogenic, radiofrequency (RF), microwave, laser, ultrasound, and pulsed electric fields. The principles of using energy to treat other pathologies are similar, and therefore the techniques used to apply the energy are similar. It is also noted that the aspects described herein may be used in vivo or in vitro.

Example Catheter Aspects

FIG. 1 illustrates a catheter 100 according to aspects of the present disclosure. Catheter 100 includes a proximal section 102, a distal section 104, and a sheath 106 coupled between proximal section 102 and distal section 104. In an aspect, sheath 106 includes one or more radiopaque markers for navigation purposes. In one aspect, catheter 100 includes a communication interface 110 between catheter 100 and a processing device 108. Communication interface 110 may include one or more optical fibers and connectors between processing device 108 and catheter 100. In other examples, communication interface 110 may include an interface component that allows wireless communication, such as Bluetooth, WiFi, cellular, and the like, to communicate with catheter 100 or other processing components in a catheter system.

In an aspect, sheath 106 and distal section 104 are disposable. As such, proximal section 102 may be reused by attaching a new sheath 106 and proximal section 104 each time a new procedure is to be performed. In another aspect, proximal section 102 is also disposable.

Proximal section 102 may house various electrical and optical components used in the operation of catheter 100. A first optical source may be included within proximal section 102 to generate a source beam of radiation for optical evaluation. The first optical source may include one or more laser diodes or light emitting diodes (LEDs). The beam of radiation generated by the optical source may have a wavelength within the infrared range. In one example, the beam of radiation has a central wavelength of 1.3 μm. The optical source may be designed to output a beam of radiation at only a single wavelength, or it may be a swept source and be designed to output a range of different wavelengths. The generated beam of radiation may be guided towards distal section 104 via the optical transmission medium connected between proximal section 102 and distal section 104 within sheath 106. Some examples of optical transmission media include single mode optical fibers and/or multimode optical fibers. In one aspect, the electrical transmission medium and the optical transmission medium are provided by the same hybrid medium allowing for both electrical and optical signal propagation.

In some aspects, proximal section 102 may include a second optical source, such as a laser energy source, to generate laser energy that is applied at distal section 104 for tissue ablation. In some aspects, the laser energy source may emit an ablation beam of laser energy at a wavelength of 980 nm or a wavelength of 1060 nm. The laser energy from the source in the proximal section 102 may propagate down the catheter 100 via an optical transmission medium connected between proximal section 102 and distal section 104 within sheath 106, and the laser energy may be output from the distal section 104 of catheter 100 to target tissue. For example, the laser energy from the source may produce an optical power of 5 W to 12 W that is applied to target tissue for 20-30 seconds to produce transmural lesions in heart tissue. In another example, the laser energy from the source may produce an optical power of 30 W to 50 W that is applied to target tissue for 60-90 seconds. In some aspects, processing device 108 may include one or more components, such as detectors, electronics, and/or other components of an optical circuit/system as described herein. In other aspects, these one or more components, such as detectors, electronics, and/or other components of an optical circuit/system may be included in the proximal section 102.

In an aspect, proximal section 102 includes one or more components of an interferometer in order to perform low coherence interferometry (LCI) using the light generated from the second optical source. Due to the nature of interferometric data analysis, in an aspect, the optical transmission medium used for guiding the light to and from distal section 104 does not affect the state and degree of light polarization. In another aspect, the optical transmission medium affects the polarization in a constant and reversible way.

Proximal section 102 may include further interface elements with which a user of catheter 100 can control the operation of catheter 100. For example, proximal section 102 may include a deflection control mechanism that controls a deflection angle of distal section 104. The deflection control mechanism may require a mechanical movement of an element on proximal section 102, or the deflection control mechanism may use electrical connections to control the movement of distal section 104. Proximal section 102 may include various buttons or switches that allow a user to control when laser energy is applied at distal section 104, or when the beams of radiation are transmitted from distal section 104, allowing for the acquisition of optical data. In some aspects, proximal section 102 may include a deflection control mechanism for controlling one or more pull wires that are coupled to the distal section 104. In some aspects, deflection control mechanism and the one or more pull wires allow for steering of the distal section of catheter 100 in order to maneuver within and target specific tissue regions for ablation.

Distal section 104 includes a plurality of optical view ports 112a-n. In some aspects, plurality of optical view ports 112a-n may be referred to herein as orifices or windows in the catheter tip. In an aspect, one or more of optical view ports 112a-n are machined into the outer body of distal section 104. Optical view ports 112a-n may be distributed over the outside of distal section 104, resulting in a plurality of distinct viewing directions. In some aspects, optical view ports 112a-n may transmit and collect light (e.g., optical signals) at various angles from the distal section 104. Optical view ports 112a-n also allow for a plurality of directions (e.g., beam directions) in which laser energy may be directed for tissue ablation through one or more of the optical view ports. In an aspect, each of the plurality of viewing directions are substantially non-coplanar. Optical view ports 112a-n may also be designed with irrigation functionality to cool distal section 104 and surrounding tissue during ablation.

Catheter optical view ports 112a-n may be components of catheter 100. Catheter optical view ports 112a-n may be used to monitor structural changes in tissue of patient 304. Catheter optical view ports 112a-n may monitor structural changes in tissue of patient 304 through a source beam of radiation. The source beam of radiation may be from an optical source in catheter 100, including one or more laser diodes or LEDs, or may be from an external signal generator, as further discussed below. The source beam may interact with a tissue of a patient. Optical transmission media may guide light reflected back from the patient's tissue, through catheter optical view ports 112a-n, towards processing device 108.

Figure 2A:
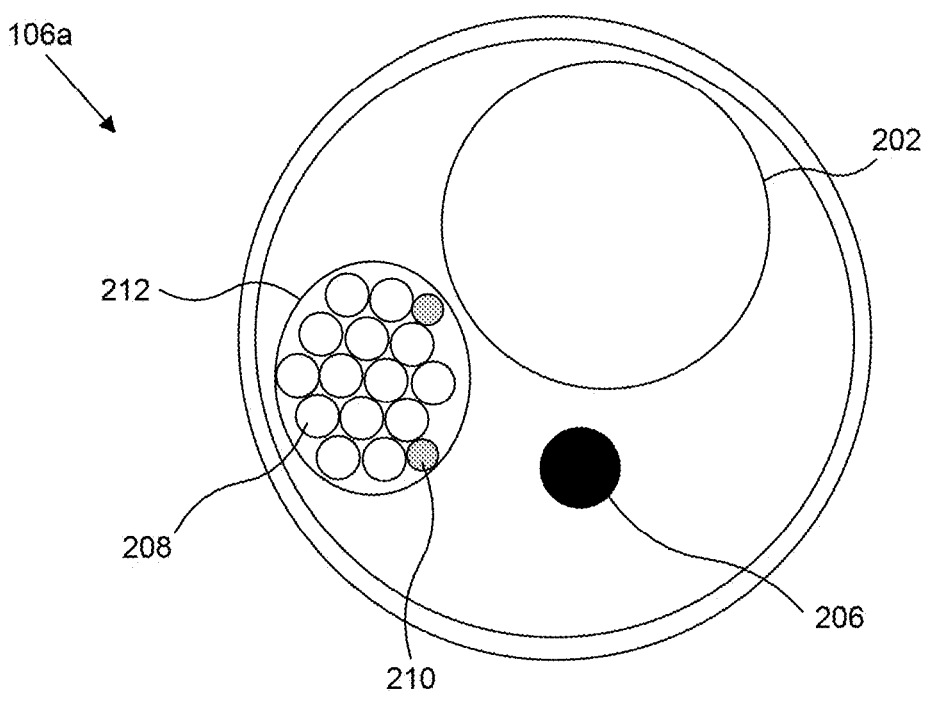
FIGS. 2A and 2B illustrate cross sections of a catheter, according to embodiments of the present disclosure.
Figure 2B:
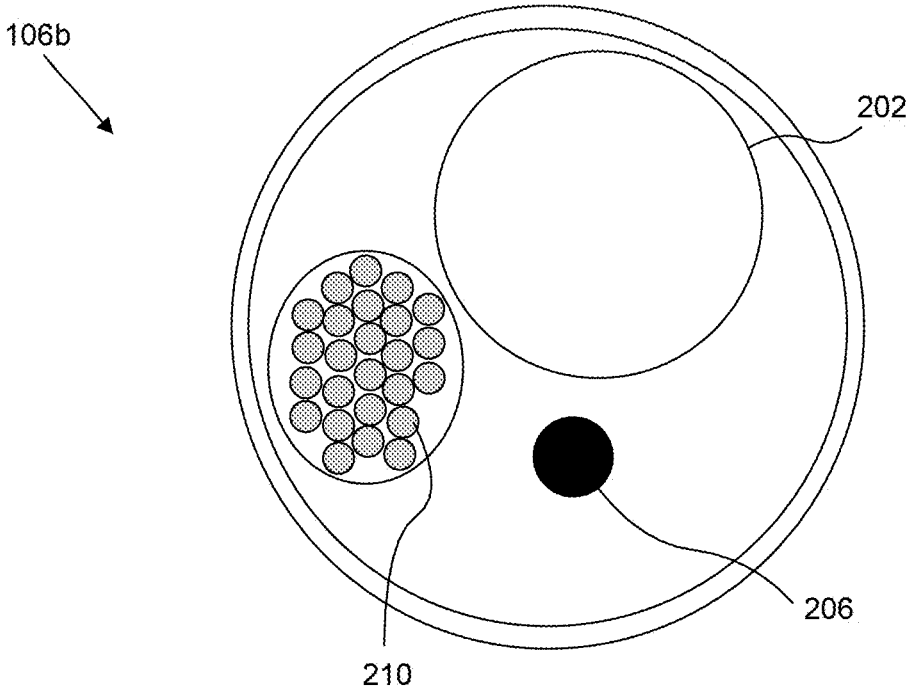

FIGS. 2A and 2B illustrate cross-section views of sheath 106, according to aspects of the present disclosure. Sheath 106 may include all of the elements interconnecting proximal section 102 with distal section 104. Sheath 106a illustrates an aspect that houses an irrigation channel 202, deflection mechanism 206, electrical connections 208, and optical transmission medium 210. FIG. 2A illustrates a protective cover 212 wrapped around both electrical connections 208 and optical transmission media 210. Electrical connections 208 may be used to provide signals to optical modulating components located in distal section 104. In other aspects, optical transmission media 212 and components may be located within a protective cover that is separate from the protective cover 212 in which the electrical connections 208 is housed. One or more optical transmission media 210 guide light generated from the optical source (exposure light) towards distal section 104, while another subset of optical transmission media 210 guides light returning from distal section 104 (scattered or reflected light) back to proximal section 102. In another example, the same one or more optical transmission media 210 guides light in both directions. In some aspects, the optical transmission medium 210 comprises one or more single mode optical fibers and/or multimode optical fibers.

Irrigation channel 202 may be a hollow tube used to guide cooling fluid towards distal section 104. Irrigation channel 202 may include heating and/or cooling elements disposed along the channel to affect the temperature of the fluid. In another aspect, irrigation channel 202 may also be used as an avenue for drawing fluid surrounding distal section 104 back towards proximal section 102.

Deflection mechanism 206 may include electrical or mechanical elements designed to provide a signal to distal section 104 in order to change a deflection angle of distal section 104. The deflection system enables guidance of distal section 104 by actuating a mechanical control placed in proximal section 102, according to an aspect. This system may be based on a series of aligned and uniformly spaced cutouts in sheath 106 aimed at providing unidirectional deflection of distal section 104, in combination with a wire which connects the deflection mechanism control in proximal section 102 with the catheter tip at distal section 104. In this way, a certain movement of the proximal section may be projected to the distal section. Other aspects involving the combination of several control wires attached to the catheter tip may enable the deflection of the catheter tip along different directions.

FIG. 2B illustrates a cross-section of sheath 106b. Sheath 106b depicts an aspect having most of the same elements as sheath 106a from FIG. 2A, except that there are no electrical connections 208. Sheath 106b may be used in situations where modulation (e.g., multiplexing) of the generated beam of radiation is performed in proximal section 102. In some aspects, sheath 106b may be implemented in a diagnostic catheter that is used for laser or cryogenic ablation.

Example Catheter System and Console Aspects

Disclosed herein are aspects of an ablation catheter and console system that uses optical coherence tomography (OCT) and/or optical coherence reflectometry (OCR), refractometry, or other methods to perform tissue ablations, track scar formation in real-time, and monitor/verify lesion geometries and isolation by directly observing the scar pattern in tissue. To assess if a scar is formed, the methods, devices, and systems described herein acquire optically reflected/refracted light from the tissue, determine optical properties of the reflected light (e.g., by measuring intensity and polarization and computing phase retardation and/or birefringence of tissue based on the measurements), and monitor changes, as these optical properties change when tissue is scarred when compared to healthy tissue. By identifying the changes in optical properties of the tissue, lesion depths and denaturation times in tissue may be predicted for various ablation times, as described herein.

Figure 3:
FIG. 3 illustrates a diagram of an example system for ablation, according to embodiments of the present disclosure.
Figure 3:
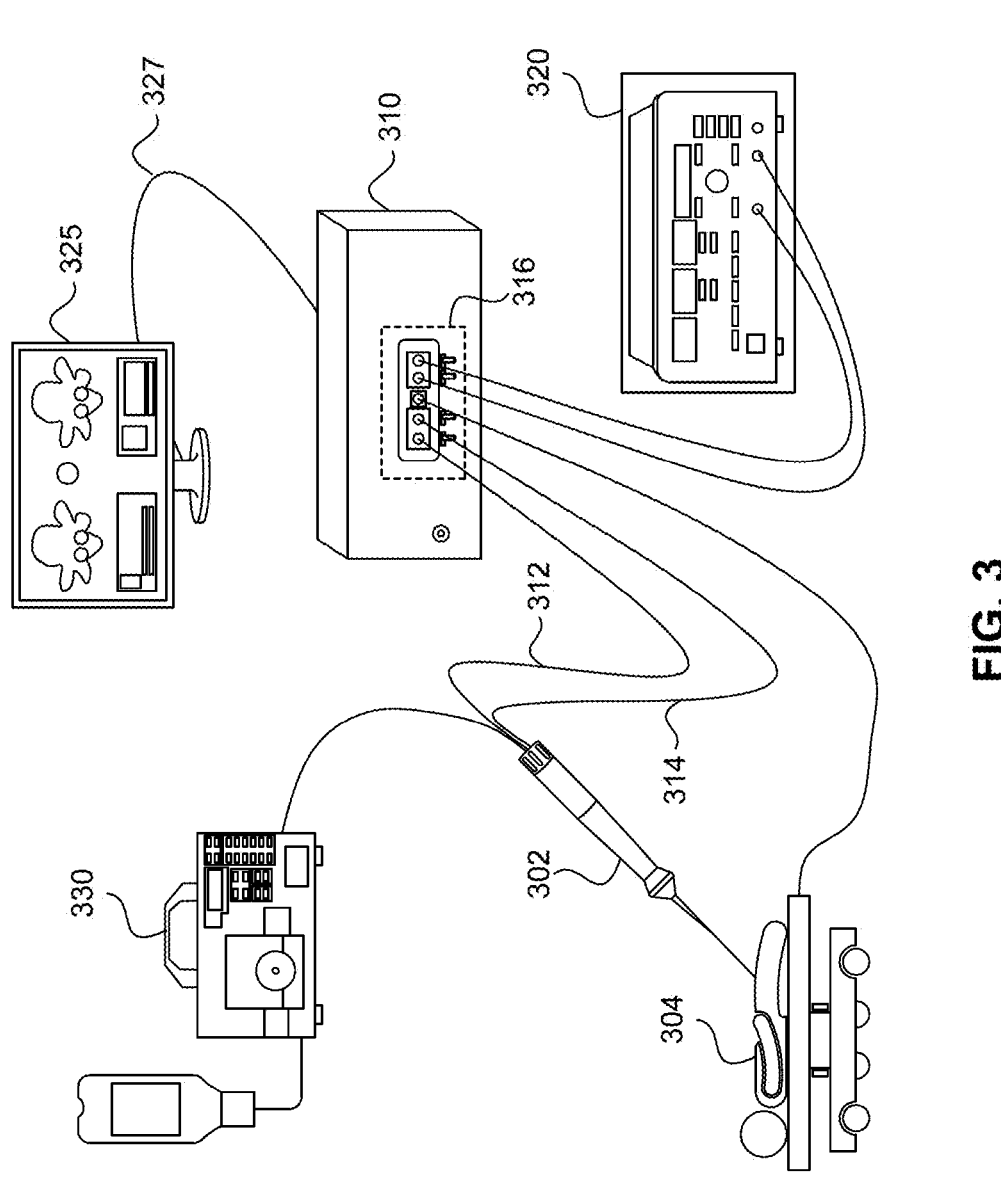

FIG. 3 illustrates an example diagram of a system 300 for performing ablation and lesion prediction, according to aspects of the present disclosure. The system 300 includes catheter 302, console 310, signal generator 320, display 325, and irrigation pump 330. The catheter 302, console 310, signal generator 320, display 325, and irrigation pump 330 may be communicatively coupled together via wired and/or wireless connections. In some aspects, catheter 302 may include catheter 100 and its features as described with respect to FIG. 1. In some aspects, a distal section of catheter 302 is positioned at a portion of tissue in patient 304. It is understood that the aspects described herein may be used in vivo and/or in vitro.

In some aspects, catheter 302 may be positioned at a portion of tissue subject to ablation using energy generated by signal generator 320. In some aspects, signal generator 320 may be an electronic device configured to generate radiofrequency (RF), cryogenic, or electroporation (e.g., pulsed electric field) signals for ablation. The signal generator 320 may be coupled to catheter 302 directly or via the console 310, and may send energy to catheter 302 to ablate the portion of tissue at a selected tissue site. In some aspects, the portion of tissue may comprise myocardial tissue, cardiac muscle tissue, skeletal tissue, or the like. Energy may be applied to the portion of tissue through optical view ports in the distal section of catheter 302. After applying the energy, structural changes in the tissue may be observed by acquiring optical signals via one or more optical view ports of catheter 302.

Console 310 may comprise a computing device configured to acquire the optical signals from catheter 302 and analyze the optical signals to detect changes in optical properties of the tissue. In some aspects, console 310 may include hardware (e.g., circuits), firmware, software, or any combination thereof to perform analysis of the optical signals and generate models for predicting lesion depths and ablation times as described herein. In some aspects, console 310 may send light through an optical circuit within itself and the catheter 302 and into the tissue to monitor scar progression, contact between the tissue and catheter 302, and other characteristics of the tissue. In some aspects, console 310 may be referred to herein as a control console, a processing device, and/or controller. Console 310 may be coupled to display 325, which may present results from the optical signal analysis and lesion predictions and allow a user to select/view, modify, and/or control parameters related to operation of catheter 302, console 310, signal generator 320, and/or irrigation pump 330.

In some aspects, irrigation pump 330 may be coupled to catheter 302 via a tubing. In some aspects, irrigation pump 330 may allow for fluid to be pumped through the tubing and released at the tissue site through catheter 302 (e.g., through optical view ports or through separate irrigation slits at the distal section of catheter 302). Fluid from the irrigation pump 330 may cool the distal section of catheter 302 and the surrounding tissue during ablation, and also flush away any debris during and/or after ablation.

In some aspects, catheter 302 may be coupled to console 310 via one or more optical connections 312 and one or more electrical connections 314. Optical connections 312 may include single mode optical fibers and/or multimode optical fibers that allow acquisition and/or transmission of optical signals to and from catheter 302 and console 310 for further analysis. Electrical connections 314 may include wiring, pins, and/or components used for supplying power and energy from signal generator 320 to catheter 302 for ablation.

In some aspects, the optical and electrical connections 312, 314 may be connected to console 310 via a communication interface 316. Communication interface 316 may allow for transmission of various signals (e.g., optical and electrical signals) between catheter 302 and console 310. In some aspects, the communication interface 316 may include a connector that facilitates proper alignment of optical fibers between the catheter 302 and console 310. In some aspects, the connector design may include both electrical and optical extension lines.

Example Acquisition and Synchronization Aspects

Figure 4:
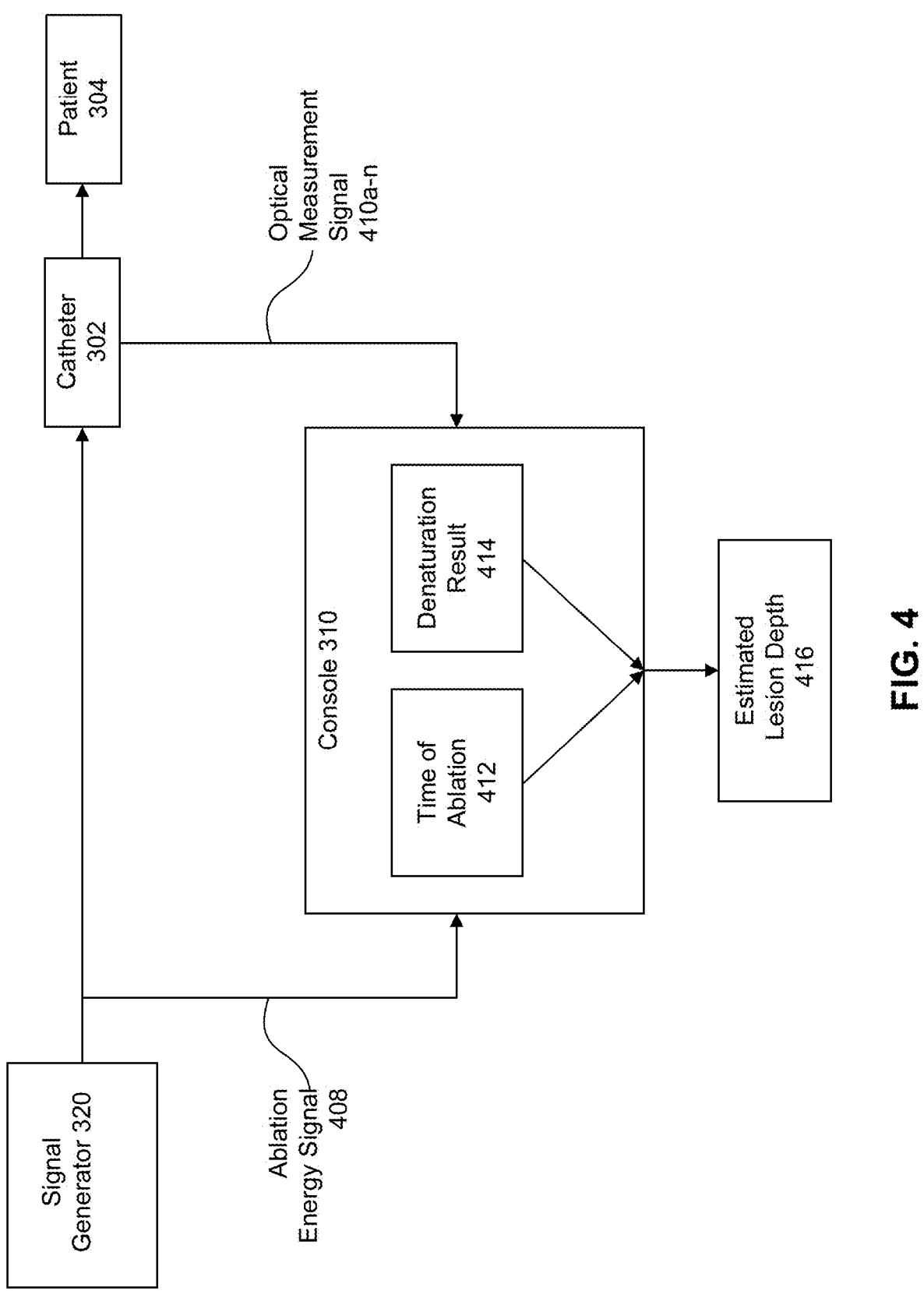
FIG. 4 is a block diagram of a system for improving the accuracy of an ablation model through synchronization, according to some aspects of the present disclosure.

FIG. 4 is a block diagram further illustrating elements of system 300 for improving the accuracy of an ablation model through synchronization, according to some aspects of the present disclosure. As discussed above, system 300 may include signal generator 320, catheter 302, and console 310. Signal generator 320 outputs ablation energy signal 408. Console 310 determines a time of ablation 412 and a denaturation result 414, which are in turn used to determine estimated lesion depth 416. Catheter 302, which outputs optical measurement signals 410a-n received from its optical ports 112a-n to console 310, may be used with patient 304. Console 310 may include hardware, firmware, software, or any combination thereof to activate signal sources (e.g., signal generator 320), acquire signals (e.g., ablation energy signal 408 or optical measurement signal 410*a-n*), assign time stamps to signals based on certain occurrences, perform analysis of signals in order to generate results (e.g., denaturation result 414), and perform synchronization of signals in order to generate a result (e.g., estimated lesion depth 416) from a synchronized model. For example, console 310 may include a clock useful for time stamping.

FIG. 5 is a timing diagram 500 including time stamps used for improving the accuracy of an ablation model through synchronization, according to some aspects of the present disclosure. Timing diagram 500 illustrates the timing of respective waveforms, where a waveform is shown with an amplitude of "1" when a signal is on or active, and the waveform is shown with an amplitude of "0" when a signal is off or inactive. Timing diagram 500 includes ablation energy signal 408, optical measurement signal 412-1, optical measurement signal 412-2, and optical measurement signal 412-3. Each optical measurement signal 410*a-n* corresponds to a signal received from one of the optical ports 112 at the distal end of catheter 302, containing information regarding the tissue of patient 304 viewable by the respective optical port 112. A person of skill in the art will recognize that more or fewer optical measurement signals 410 may be included in timing diagram 500 based on the number of optical ports 112*a-n* at the distal end of catheter 302.

As illustrated in timing diagram 500, console 310 may use its clock to assign a time stamp to ablation energy signal 408 when signal generator 320 is activated (1) (shown in the example of FIG. 5 as time=0 ms). This time stamp may be considered an activation time stamp. Console 310 may also assign a time stamp to ablation energy signal 408 when signal generator 320 is deactivated (0) (shown in the example of FIG. 5 as time=10 ms). This time stamp may be considered a deactivation time stamp. Console 310 may reactivate signal generator 320 and assign a time stamp to ablation energy signal 408 when signal generator 320 is reactivated (1) (shown in the example of FIG. 5 as time=12 ms). This time stamp may be considered a subsequent activation time stamp. Console 310 may assign a time stamp to ablation energy signal 408 when signal generator 320 is deactivated (0) after reactivation. This time stamp may be considered a subsequent deactivation time stamp.

Console 310 may determine a time period between each activation time stamp and deactivation time stamp pairing. This time period may be considered a time of ablation because it reflects the time that signal generator 320 was activated in order to provide an energy for ablation of a tissue of patient 304. Where there are multiple activations, any subsequent activation time period may be added to the time of ablation to determine a total time period. This total time period may be considered a total time of ablation because it reflects the total time that signal generator 320 was activated in order to provide an energy for ablation of a tissue of patient 304.

Console 310 may acquire optical measurement signal 410-1 from a catheter optical port 112*a*. Catheter optical port 112*a* may have a unique viewing angle of the tissue of patient 304. The unique viewing angle may view a first location of the tissue of patient 304. Console 310 may acquire optical measurement signal 410-1 through catheter 302 and optical connection 312. As illustrated in timing diagram 500, console 310 may assign a time stamp to optical measurement signal 410-1 when optical measurement signal 410-1 is first acquired (1) from catheter optical port 112*a*. This time stamp may be considered an input time stamp. Console 310 may assign a time stamp to optical measurement signal 410-1 when optical measurement signal 410-1 is no longer being acquired (0) from catheter optical port 112*a*, such as when console 310 switches its inputs from catheter optical port 112*a* to a different catheter optical port, such as catheter optical port 112*b*. This time stamp may be considered a switching time stamp.

Once console 310 switches its input from catheter optical port 112*a* to catheter optical port 112*b*, console 310 may acquire optical measurement signal 410-2 from catheter optical port 112*b*. Optical measurement signal 410-2 may be considered a subsequent optical measurement signal 410*a-n* and catheter optical port 112*b* may be considered a different catheter optical port in optical ports 112*a-n*. In an aspect, after signal acquisition from catheter optical port 112*a* has completed, an optical switch at console 310 may close the connection with catheter optical port 112*a* and open a connection with catheter optical port 112*b*, so that optical measurement signal 410-2 from catheter optical port 112*b* may be acquired by console 310. This switch may occur at a predetermined time period after data collection from catheter optical port 112*a* begins. According to some aspects, the predetermined time period may be selected based on the amount of time it takes to obtain sufficient data from which an optical property corresponding to optical port 112*a*'s field of view may be determined. For example, the predetermined time period may be 2 milliseconds. In another example, the predetermined time period may be 1 millisecond. In yet another example, the predetermined time period may be another time period less than or more than 2 milliseconds.

Catheter optical port 112*b* may have a unique viewing angle of the tissue of patient 304. The unique viewing angle may view a second location of the tissue of patient 304. Console 310 may acquire optical measurement signal 410-2 through catheter 302 and optical connection 312. As illustrated in timing diagram 500, console 310 may assign a time stamp to optical measurement signal 410-2 when optical measurement signal 410-2 is first acquired (1) from catheter optical port 112*b*. This time stamp may be considered a subsequent input time stamp. Console 310 may assign a time stamp to optical measurement signal 410-2 when optical measurement signal 410-2 is no longer being acquired (0) from catheter optical port 112*b*, such as when console 310 switches its input from catheter optical port 112*b* to a different catheter optical port, such as catheter optical port 112*c*. This time stamp may be considered a subsequent switching time stamp.

Similar time-stamping actions may be taken on other signals received from catheter 302, such as optical measurement signal 410-2, optical measurement signal 410-3, etc.

Console 310 may include an optical system to process optical measurement signals 410*a-n*, to calculate optical properties, to acquire denaturation result 414, or to generate graphical representations (e.g., estimated lesion depth 416). The optical system may utilize low-coherence interferometry (LCI), optical coherence tomography (OCT), optical coherence refractometry (OCR), or other optical modalities to perform imaging and to obtain optical measurement signal 410*a-n*. Optical measurement signal 410*a-n* may be an OCT signal, an OCR signal, or another signal that would be appreciated by a person of ordinary skill in the art.

Console 310 may include an optical system to process optical measurement signal 410-1 and/or optical measurement signal 410-2 in order to acquire denaturation result 414. Console 310 may implement a process on optical measurement signal 410-1 and/or optical measurement signal 410-2 in order to acquire denaturation result 114. Console 310 may implement a process on optical measurement signal 410-1 and/or optical measurement signal 410-2 in order to obtain an optical property of the tissue of patient 304 at the first location and/or the second location in order to obtain denaturation result 414.

The process may be optimized in different software layers. The process may include optimization algorithms in order to optimize the quality of information. The optimization algorithms may rearrange data, remove glitches in data, conduct a Hilbert transform on data, remove phase noise from data, linearize phase of data, compensate for polarization mode of data, conduct a Fourier transform on data, or conduct other processing of data. Optical properties may include polarization and/or birefringence. Birefringence, or a loss of birefringence, may be correlated with necrosis and muscle fiber denaturation. Optical properties may include spectral information and/or other properties that would be appreciated by a person of ordinary skill in the art. Denaturation result 414 may represent a denaturation time.

Console 310 may synchronize time of ablation 412 and denaturation result 414 in order to generate a synchronized model. Console 310 may synchronize time of ablation 412 and denaturation result 414 using the activation time stamp, deactivation time stamp, input time stamp, or switching time stamp in order to generate a synchronized model. Console 310 may also synchronize time of ablation 412 and denaturation result 414 using the subsequent activation time stamp, subsequent deactivation time stamp, subsequent input time stamp, or subsequent switching time stamp from any or all of optical measurement signals 410*a-n* in order to generate a synchronized model. Console 310 may synchronize time of ablation 412 and denaturation result 414 by associating 1's and 0's, as illustrated by timing diagram 500. The synchronized model may reflect an association between when energy is being applied to tissue of patient 304 and when structural changes are occurring in tissue of patient 304.

As illustrated by FIG. 5, console 310 may switch between various optical ports 112*a-n* to obtain respective optical measurement signals 410*a-n* while signal generator 320 is actively generating ablation optical signal 408. The timestamps added by console 310 to each optical signal 408 and 410*a-n* allow denaturation results 414 to be repeatedly and consistently determined throughout ablation and mapped to the ablation optical signal 408.

Console 310 may generate a graphical representation from the synchronized model. A graphical representation may illustrate or identify, for example, estimated lesion depth 416 at a particular area of tissue of patient 304 as determined using, for example, each measurement optical signal 410*a-n* from a respective optical port 112*a-n*. Estimated lesion depth 416 may be a function of time of ablation 412 over denaturation result 414. Estimated lesion depth 416 may represent a height and a width of a lesion formed by the energy applied by signal generator 320 to a tissue of patient 304. By providing synchronized observations from measurement optical signals 410*a-n* throughout ablation, a more accurate depiction of ablation results can be provided and displayed to a user.

The tissue of patient 304 may comprise myocardial tissue, cardiac muscle tissue, skeletal tissue, or the like. An example study was conducted in order to develop a lesion depth estimation algorithm using optical property measurements from ablated tissue. In the study, tissue samples were excised from swine hearts, and an end of the catheter was perpendicularly positioned at the endocardial surface of the tissue using a micropositioner. The tissue samples included right atrial free wall, superior vena cava, left atrial roof, mitral annulus, and left atrial appendage. In aspects, graphical representations may be other representations that would be appreciated by a person of ordinary skill in the art.

Returning to FIG. 3, console 310 may interface display 325 through communications channel 327. Communications channel 327 may be wired, wireless, or a combination thereof. Communications channel 327 may include optical connections or electrical connections. Optical connections may include single mode optical fibers or multimode optical fibers that allow acquisition or transmission of optical signals, and electrical connections may include wiring, pins, or components used for supplying power and energy. Communications channel 208 may include any combination of Local Area Networks, Wide Area Networks, the Internet, etc. Control logic or data may be transmitted to and from console 310 via communications channel 327.

Console 310 may provide display information to display 325. Display information may include ablation energy signal 408, optical measurement signals 410*a-n*, optical properties, time of ablation 412, denaturation result 414, graphical representations (e.g., estimated lesion depth 416), or other information. Display information may include contact information of catheter 302 (i.e., whether catheter 302 is sufficiently contacting the tissue) and/or other information useful for a user of display 325. Display 325 may include a graphical user interface (GUI). The GUI may include a front view of a tip of catheter 302 showing different sections that correspond to catheter optical ports 112*a-n*. The GUI may show which catheter optical ports 112*a-n* are in contact with tissue of patient 304 and which beams from catheter optical ports 112*a-n* are in operation.

The GUI may include a plurality of tiles, each tile showing an optical readout for a respective catheter optical port 112*a-n*. The number of tiles displayed corresponds to the number of catheter optical ports 112*a-n*. Each tile may represent an image resulting from processing, by console 310. Individual tiles may be switched on or off, and thus may appear or disappear, based on activity.

The GUI may also include one or more charts illustrating ablation energy data, birefringence data, phase data, and/or estimated lesion depth 416. The GUI may include a panel or indicator showing the occurrence of stable contact between catheter 302 or catheter optical ports 112*a-n* and tissue of patient 304, loss in birefringence, status of the ablation energy (e.g., activated or deactivated), and estimated lesion depth 416. The GUI may include a button or a text box allowing user selection or customization of parameters selected for ablation or for operating catheter 302 during ablation.

Because the ablation energy signal 408 has been synchronized with optical data from optical measurement signals 410*a-n*, display 325 provides a viewer, such as a surgeon, with more accurate feedback regarding the results of ablation at a given time than was previously available.

Figure 6:
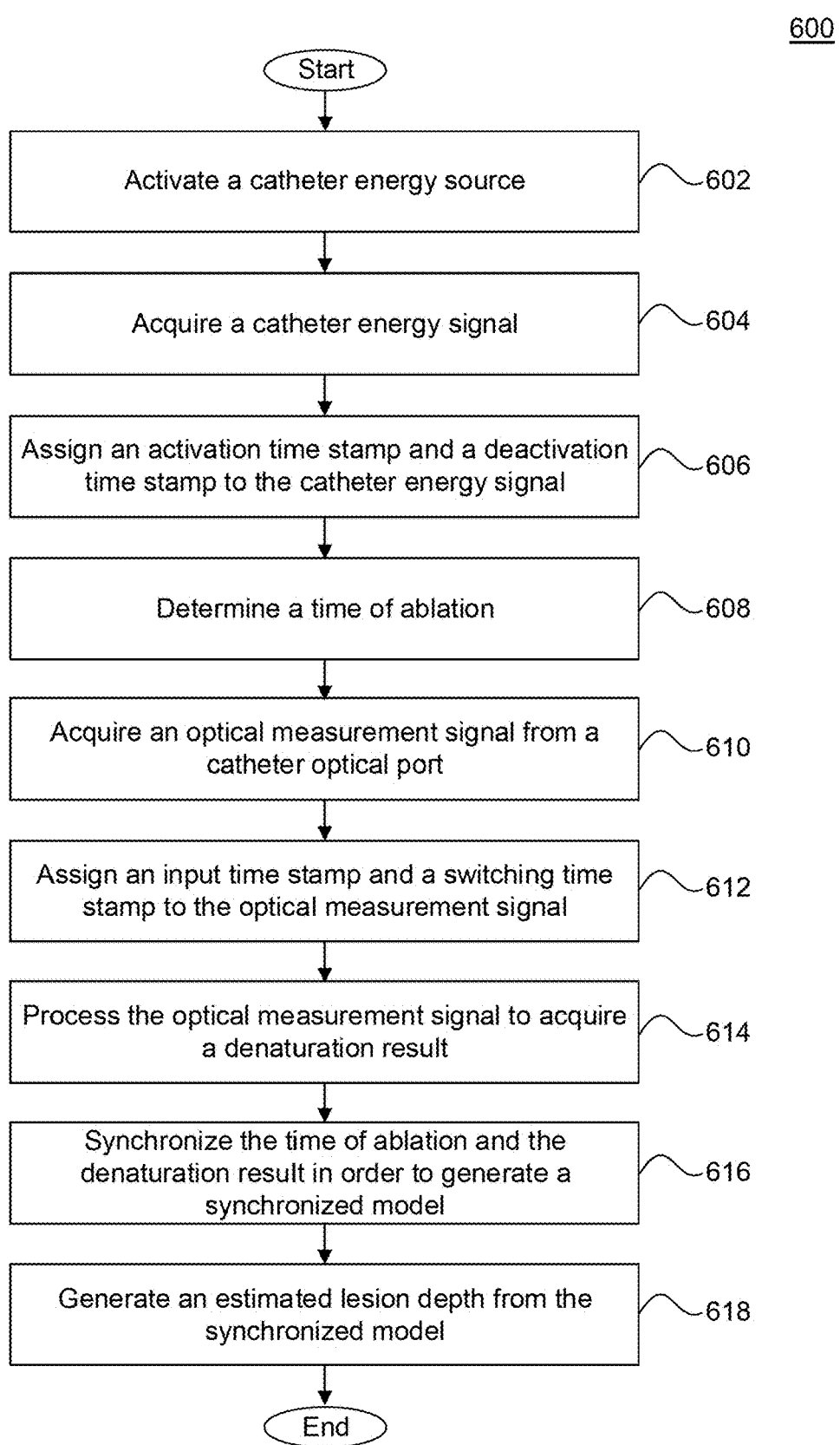
FIG. 6 is a flowchart of a method for improving the accuracy of an ablation model through synchronization, according to some aspects of the present disclosure.

FIG. 6 is a flowchart of a method 600 for improving the accuracy of an ablation model through synchronization, according to an aspect of the invention. Method 600 can be performed by processing logic that can comprise hardware (e.g., circuitry, dedicated logic, programmable logic, microcode, etc.), software (e.g., instructions executing on a processing device), or a combination thereof. It is to be appreciated that not all steps may be needed to perform the disclosure provided herein. Further, some of the steps may be performed simultaneously, or in a different order than shown in FIG. 6, as will be understood by a person of ordinary skill in the art.

Method 600 shall be described with reference to FIGS. 1-5. However, method 600 is not limited to those example aspects.

In 602, an ablation energy source is activated. In an example, console 310 activates signal generator 320. Console 310 may activate signal generator 320 in order to provide ablation energy to catheter 302 for ablation of a tissue of patient 304. Signal generator 320 may be a device configured to generate energy, such as radiofrequency (RF), cryogenic, laser, electroporation (e.g., pulsed electric field), or another form of energy.

In 604, a catheter energy signal is acquired from the ablation energy source. In an example, console 310 acquires ablation energy signal 408 from signal generator 320. Console 310 may collect ablation energy signal 408 as it is provided to catheter 302 from signal generator 320.

In 606, an activation time stamp is assigned to the ablation energy signal when the ablation energy source is activated in 602, and a deactivation time stamp is assigned to the catheter energy signal when the catheter energy source is deactivated. For example, console 310 assigns an activation time stamp to ablation energy signal 408 when signal generator 320 is activated by console 310 in 602, and a deactivation time stamp to ablation energy signal 408 when signal generator 320 is deactivated by console 310, as described above with respect to FIG. 5.

In 608, a time of ablation is determined based on a time period between the activation time stamp and the deactivation time stamp from 606. In an example, console 310 determines time of ablation 412 based on a time period between the activation time stamp and the deactivation time stamp from 606.

The time of ablation may reflect the time that signal generator 320 was activated in order to provide an energy for ablation of a tissue of patient 304.

Console 310 may determine a subsequent time period between a subsequent activation time stamp and a subsequent deactivation time stamp. This subsequent time period may be added to the previous time period in order to determine a total time period. This total time period may be considered the time of ablation because it reflects the total time that signal generator 320 was activated in order to provide an energy for ablation of a tissue of patient 304.

In 610, an optical measurement signal is acquired from a catheter optical port. In an example, console 310 acquires optical measurement signals 410-*a-n* from catheter optical port 112*a*.

Optical measurement signals 410*a-n* may include measurements from the light reflected from the tissue of patient 304 and guided back towards console 310 through transmission media in catheter 302. Each of catheter optical ports 112*a-n* can be switched on or off using console 310 in order to acquire a respective optical measurement signal 410*a-n* at different times. A catheter optical port 112*a-n* may be considered "on" or "open" when an optical switch at console 310 allows a respective optical measurement signal 410*a-n* to be acquired. A catheter optical port 112*a-n* may be considered "off" or "closed" when an optical switch at console 310 does not allow respective optical measurement signal 410*a-n* to be acquired.

A given catheter optical port 112*a* may have a unique viewing angle of the tissue of patient 304. The unique viewing angle may view a first location of the tissue of patient 304. Console 310 may acquire optical measurement signal 410-1 from catheter optical port 112*a* through catheter 302 and optical connection 312.

An existence of multiple distinct ports in catheter optical ports 112*a-n* may result in multiple distinct optical measurement signals 410*a-n* being acquired by console 310. Console 310 may acquire subsequent optical measurement signals 410, for example, optical measurement signal 410-2 from other catheter optical ports 112. For example, console 310 may acquire optical measurement signal 410-2 from catheter optical port 112*b* at a predetermined time after acquiring optical measurement signal 410-1 from catheter optical port 112*a*. For example, the predetermined time may be 2 milliseconds. In another example, the predetermined time may be 1 millisecond. In yet another example, the predetermined time may be another time period less than 2 milliseconds. In order to acquire optical measurement signal 410-2 from catheter optical port 112*b*, console 310 may switch an input from catheter optical port 112*a* to catheter optical port 112*b* after the predetermined time has passed.

Catheter optical port 112*b* may have a unique viewing angle of the tissue of patient 304. The unique viewing angle may view a second location of the tissue of patient 304. Console 310 may acquire optical measurement signal 410-2 through catheter 302 and optical connection 312.

In 612, an input time stamp is assigned to the optical measurement signal when it is first acquired from the catheter optical port in 610 and a switching time stamp is assigned to the optical measurement signal when it is no longer being acquired from the catheter optical port. In an example, console 310 assigns an input time stamp to optical measurement signal 410-1 when optical measurement signal 410-1 is first acquired from catheter optical port 112*a* in 610, and a switching time stamp to optical measurement signal 410-1 when optical measurement signal 410-1 is no longer being acquired from catheter optical port 112*a*, as illustrated in timing diagram 500.

In 614, the optical measurement signal from 610 is processed in order to acquire a denaturation result. In an example, console 302 processes optical measurement signals 410*a-n* from 510 in order to acquire denaturation result 414.

In 616, the time of ablation from 608 and the denaturation result from 614 are synchronized using the activation time stamp and deactivation time stamp from 606 and the input time stamp and switching time stamp from 612, in order to generate a synchronized model. In an example, console 310 synchronizes time of ablation 412 from 608, and denaturation result 414 from 614 using the activation time stamp and deactivation time stamp from 606 and the input time stamp and switching time stamp from 612, in order to generate a synchronized model.

Console 310 may also synchronize time of ablation 412 and denaturation result 414 using the subsequent activation time stamp, subsequent deactivation time stamp, subsequent input time stamp, or subsequent switching time stamp in order to generate a synchronized model. Console 310 may synchronize time of ablation 412 and denaturation result 414 by associating activation and deactivation timestamps (e.g., changes between 1's and 0's, as illustrated by timing diagram 500). The synchronized model may reflect an association between times when energy is being applied to tissue of patient 304 and when structural changes are occurring in tissue of patient 304.

In 618, an estimated lesion depth is generated from the synchronized model in 616. In an example, console 310 generates estimated lesion depth 416 from the synchronized model from 616.

Estimated lesion depth 416 may be a function of time of ablation 412 over denaturation result 414. Estimated lesion depth 416 may represent a height and a width of a lesion formed by the energy applied by signal generator 320 to a tissue of patient 304.

Console 310 may provide estimated lesion depth 416 and/or a graphical representation thereof to display 325. Display 325 may display estimated lesion depth 416 and/or a graphical representation thereof. Display 325 may include a graphical user interface (GUI).

Figure 7:
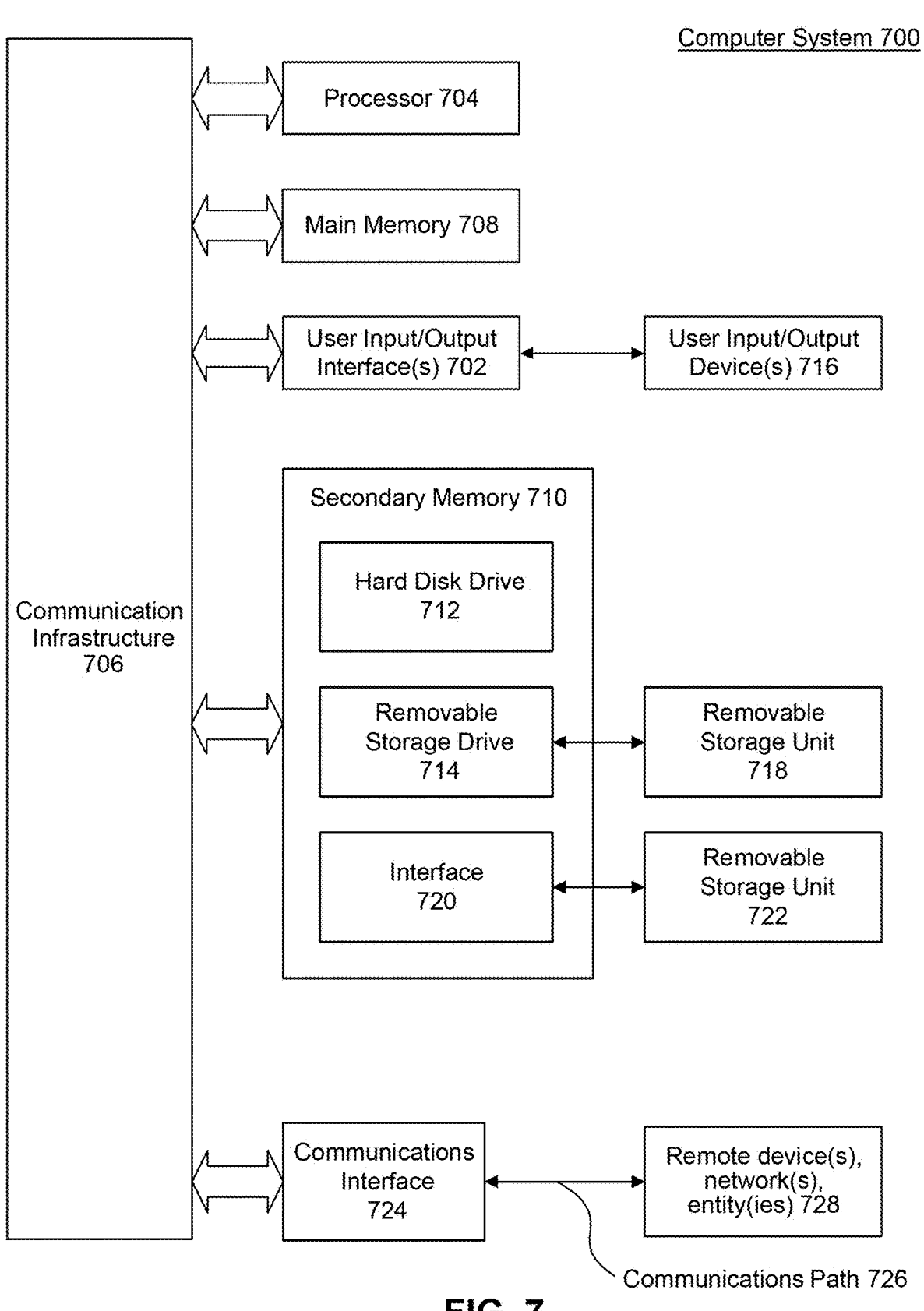
FIG. 7 is a block diagram of an example computer system useful for implementing various aspects.

Various aspects can be implemented, for example, using one or more computer systems, such as computer system 700 shown in FIG. 7. Computer system 700 can be used, for example, to implement method 600 of FIG. 6, console 310 of FIG. 3, and the like. For example, computer system 700 can assign time stamps to various signals in order to generate a synchronized model. Computer system 700 can also generate an estimated lesion depth from the synchronized model, according to some aspects. Computer system 700 can be any computer capable of performing the functions described herein.

Computer system 700 includes one or more processors (also called central processing units, or CPUs), such as a processor 704. Processor 704 is connected to a communication infrastructure or bus 706.

One or more processors 704 may each be a graphics processing unit (GPU). In an aspect, a GPU is a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 700 also includes user input/output device(s) 716, such as monitors, keyboards, pointing devices, etc., that communicate with communication infrastructure 706 through user input/output interface(s) 702.

Computer system 700 also includes a main or primary memory 708, such as random access memory (RAM). Main memory 708 may include one or more levels of cache. Main memory 708 has stored therein control logic (i.e., computer software) and/or data.

Computer system 700 may also include one or more secondary storage devices or memory 710. Secondary memory 710 may include, for example, a hard disk drive 712 and/or a removable storage device or drive 714. Removable storage drive 714 may be a floppy disk drive, a magnetic tape drive, a compact disk drive, an optical storage device, tape backup device, and/or any other storage device/drive.

Removable storage drive 714 may interact with a removable storage unit 718. Removable storage unit 718 includes a computer usable or readable storage device having stored thereon computer software (control logic) and/or data. Removable storage unit 718 may be a floppy disk, magnetic tape, compact disk, DVD, optical storage disk, and/any other computer data storage device. Removable storage drive 714 reads from and/or writes to removable storage unit 718 in a well-known manner.

According to an exemplary aspect, secondary memory 710 may include other means, instrumentalities or other approaches for allowing computer programs and/or other instructions and/or data to be accessed by computer system 700. Such means, instrumentalities or other approaches may include, for example, a removable storage unit 722 and an interface 720. Examples of the removable storage unit 722 and the interface 720 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 700 may further include a communication or network interface 724. Communication interface 724 enables computer system 700 to communicate and interact with any combination of remote devices, remote networks, remote entities, etc. (individually and collectively referenced by reference number 728). For example, communication interface 724 may allow computer system 700 to communicate with remote devices 728 over communications path 726, which may be wired and/or wireless, and which may include any combination of LANs, WANs, the Internet, etc. Control logic and/or data may be transmitted to and from computer system 700 via communication path 726.

In an aspect, a tangible, non-transitory apparatus or article of manufacture comprising a tangible, non-transitory computer useable or readable medium having control logic (software) stored thereon is also referred to herein as a computer program product or program storage device. This includes, but is not limited to, computer system 700, main memory 708, secondary memory 710, and removable storage units 718 and 722, as well as tangible articles of manufacture embodying any combination of the foregoing. Such control logic, when executed by one or more data processing devices (such as computer system 700), causes such data processing devices to operate as described herein.

Based on the teachings contained in this disclosure, it will be apparent to persons skilled in the relevant art(s) how to make and use aspects of this disclosure using data processing devices, computer systems and/or computer architectures other than that shown in FIG. 7. In particular, aspects can operate with software, hardware, and/or operating system implementations other than those described herein.

It is to be appreciated that the Detailed Description section, and not any other section, is intended to be used to interpret the claims. Other sections can set forth one or more but not all exemplary aspects as contemplated by the inventor(s), and thus, are not intended to limit this disclosure or the appended claims in any way.

While this disclosure describes exemplary aspects for exemplary fields and applications, it should be understood that the disclosure is not limited thereto. Other aspects and modifications thereto are possible, and are within the scope and spirit of this disclosure. For example, and without limiting the generality of this paragraph, aspects are not limited to the software, hardware, firmware, and/or entities illustrated in the figures and/or described herein. Further, aspects (whether or not explicitly described herein) have significant utility to fields and applications beyond the examples described herein.

Aspects have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative aspects can perform functional blocks, steps, operations, methods, etc. using orderings different than those described herein.

References herein to "one aspect," "an aspect," "an example aspect," or similar phrases, indicate that the aspect described can include a particular feature, structure, or characteristic, but every aspect can not necessarily include the particular feature, structure, or characteristic. Moreover, such phrases are not necessarily referring to the same aspect.

Further, when a particular feature, structure, or characteristic is described in connection with an aspect, it would be within the knowledge of persons skilled in the relevant art(s) to incorporate such feature, structure, or characteristic into other aspects whether or not explicitly mentioned or described herein. Additionally, some aspects can be described using the expression "coupled" and "connected" along with their derivatives. These terms are not necessarily intended as synonyms for each other. For example, some aspects can be described using the terms "connected" and/or "coupled" to indicate that two or more elements are in direct physical or electrical contact with each other. The term "coupled," however, can also mean that two or more elements are not in direct contact with each other, but yet still co-operate or interact with each other.

The breadth and scope of this disclosure should not be limited by any of the above-described exemplary aspects, but should be defined only in accordance with the following claims and their equivalents.

What is claimed is:

1. A computer implemented method for improving the accuracy of an ablation model through synchronization, comprising:

activating, by at least one processor, a catheter energy source;

acquiring, by the at least one processor, a catheter energy signal from the catheter energy source;

assigning, by the at least one processor, an activation time stamp to the catheter energy signal when the catheter energy source is activated and a deactivation time stamp to the catheter energy signal when the catheter energy source is deactivated;

determining, by the at least one processor, a time of ablation based on a time period between the activation time stamp and the deactivation time stamp;

acquiring, by the at least one processor, an optical measurement signal from a catheter optical port;

assigning, by the at least one processor, an input time stamp to the optical measurement signal when the optical measurement signal is first acquired from the catheter optical port and a switching time stamp to the optical measurement signal when the optical measurement signal is no longer being acquired from the catheter optical port;

processing, by the at least one processor, the optical measurement signal in order to acquire a denaturation result;

synchronizing, by the at least one processor, the time of ablation and the denaturation result using the activation time stamp, deactivation time stamp, input time stamp, and switching time stamp in order to generate a synchronized model; and generating, by the at least one processor, an estimated lesion depth from the synchronized model.

2. The computer implemented method of claim 1, the assigning an activation time stamp further comprising:

assigning a subsequent activation time stamp to the catheter energy signal when the catheter energy source is reactivated and a subsequent deactivation time stamp to the catheter energy signal when the catheter energy source is deactivated, wherein the subsequent activation time stamp and the subsequent deactivation time stamp are also used when determining and synchronizing.

3. The computer implemented method of claim 2, the determining further comprising:

determining a time of ablation based on a time period between the activation time stamp and the deactivation time stamp and a subsequent time period between the subsequent activation time stamp and the subsequent deactivation time stamp, wherein the time of ablation is also used when synchronizing.

4. The computer implemented method of claim 1, further comprising:

acquiring, by the at least one processor, a subsequent optical measurement signal from a different catheter optical port after a predetermined time of acquiring the optical measurement signal.

5. The computer implemented method of claim 4, further comprising:

assigning, by the at least one processor, a subsequent input time stamp to the subsequent optical measurement signal when the subsequent optical measurement signal is first acquired from the different catheter optical port and a subsequent switching time stamp to the subsequent optical measurement signal when the subsequent optical measurement signal is no longer being acquired from the different catheter optical port, wherein the subsequent input time stamp and the subsequent switching time stamp are also used when synchronizing.

6. The computer implemented method of claim 4, the processing further comprising:

processing the optical measurement signal and the subsequent optical measurement signal in order to acquire a denaturation result, wherein the denaturation result is also used when synchronizing.

7. The computer implemented method of claim 4, further comprising:

switching, by the at least one processor, an input of the at least one processor from the catheter optical port to the different catheter optical port after the predetermined time.

8. The computer implemented method of claim 4, wherein the predetermined time is 2 milliseconds.

9. The computer implemented method of claim 4, wherein the predetermined time is 1 millisecond.

10. The computer implemented method of claim 1, the processing further comprising:

calculating birefringence, polarization, phase retardation, or another optical property of a tissue from the optical measurement signal in order to acquire the denaturation result.

11. The computer implemented method of claim 1, further comprising:

displaying, by the at least one processor, the estimated lesion depth on a user interface.

12. A system for improving the accuracy of an ablation model through synchronization, comprising:

a catheter energy source;

a catheter coupled to the catheter energy source, comprising a catheter optical port; and a computing device coupled to the catheter energy source and the catheter, the computing device comprising:

a processor; and a memory, wherein the memory contains instructions stored thereon that when executed by the processor cause the computing device to:

activate the catheter energy source;

acquire a catheter energy signal from the catheter energy source;

assign an activation time stamp to the catheter energy signal when the catheter energy source is activated and a deactivation time stamp to the catheter energy signal when the catheter energy source is deactivated;

determine a time of ablation based on a time period between the activation time stamp and the deactivation time stamp;

acquire an optical measurement signal from the catheter optical port;

assign an input time stamp to the optical measurement signal when the optical measurement signal is first acquired from the catheter optical port and a switching time stamp to the optical measurement signal when the optical measurement signal is no longer being acquired from the catheter optical port;

process the optical measurement signal in order to acquire a denaturation result;

synchronize the time of ablation and the denaturation result using the activation time stamp, deactivation time stamp, input time stamp, and switching time stamp in order to generate a synchronized model; and generate an estimated lesion depth from the synchronized model.

13. The system of claim 12, wherein to assign an activation time stamp, the memory contains further instructions stored thereon that when executed by the processor cause the computing device to:

assign a subsequent activation time stamp to the catheter energy signal when the catheter energy source is reactivated and a subsequent deactivation time stamp to the catheter energy signal when the catheter energy source is deactivated, wherein the subsequent activation time stamp and the subsequent deactivation time stamp are also used when determining and synchronizing.

14. The system of claim 13, wherein to determine, the memory contains further instructions stored thereon that when executed by the processor cause the computing device to:

determine a time of ablation based on a time period between the activation time stamp and the deactivation time stamp and a subsequent time period between the subsequent activation time stamp and the subsequent deactivation time stamp, wherein the time of ablation is also used when synchronizing.

15. The system of claim 12, wherein the memory contains further instructions stored thereon that when executed by the processor cause the computing device to:

acquire a subsequent optical measurement signal from a different catheter optical port after a predetermined time of acquiring the optical measurement signal.

16. The system of claim 15, wherein the memory contains further instructions stored thereon that when executed by the processor cause the computing device to:

assign a subsequent input time stamp to the subsequent optical measurement signal when the subsequent optical measurement signal is first acquired from the different catheter optical port and a subsequent switching time stamp to the subsequent optical measurement signal when the subsequent optical measurement signal is no longer being acquired from the different catheter optical port, wherein the subsequent input time stamp and the subsequent switching time stamp are also used when synchronizing.

17. The system of claim 15, wherein to process, the memory contains further instructions stored thereon that when executed by the processor cause the computing device to:

process the optical measurement signal and the subsequent optical measurement signal in order to acquire a denaturation result, wherein the denaturation result is also used when synchronizing.

18. The system of claim 15, wherein the memory contains further instructions stored thereon that when executed by the processor cause the computing device to:

switch an input of the processor from the catheter optical port to the different catheter optical port after the predetermined time.

19. The system of claim 15, wherein the predetermined time is 2 milliseconds.

20. The system of claim 15, wherein the predetermined time is 1 millisecond.

21. The system of claim 12, wherein to process, the memory contains further instructions stored thereon that when executed by the processor cause the computing device to:

calculate birefringence, polarization, phase retardation, or another optical property of a tissue from the optical measurement signal in order to acquire the denaturation result.

22. The system of claim 12, wherein the memory contains further instructions stored thereon that when executed by the processor cause the computing device to:

display the estimated lesion depth on a user interface.

23. A non-transitory computer-readable medium having instructions stored thereon that, when executed by at least one computing device, cause the at least one computing device to perform operations comprising:

activating a catheter energy source;

acquiring a catheter energy signal from the catheter energy source;

assigning an activation time stamp to the catheter energy signal when the catheter energy source is activated and a deactivation time stamp to the catheter energy signal when the catheter energy source is deactivated;

determining a time of ablation based on a time period between the activation time stamp and the deactivation time stamp;

acquiring an optical measurement signal from a catheter optical port;

assigning an input time stamp to the optical measurement signal when the optical measurement signal is first acquired from the catheter optical port and a switching time stamp to the optical measurement signal when the optical measurement signal is no longer being acquired from the catheter optical port;

processing the optical measurement signal in order to acquire a denaturation result;

synchronizing the time of ablation and the denaturation result using the activation time stamp, deactivation time stamp, input time stamp, and switching time stamp in order to generate a synchronized model; and generating an estimated lesion depth from the synchronized model.

24. The non-transitory computer-readable medium of claim 23, wherein the assigning an activation time stamp further comprises:

assigning a subsequent activation time stamp to the catheter energy signal when the catheter energy source is reactivated and a subsequent deactivation time stamp to the catheter energy signal when the catheter energy source is deactivated, wherein the subsequent activation time stamp and the subsequent deactivation time stamp are also used when determining and synchronizing.

25. The non-transitory computer-readable medium of claim 24, wherein the determining further comprises:

determining a time of ablation based on a time period between the activation time stamp and the deactivation time stamp and a subsequent time period between the subsequent activation time stamp and the subsequent deactivation time stamp, wherein the time of ablation is also used when synchronizing.

26. The non-transitory computer-readable medium of claim 23, wherein the operations further comprise:

acquiring a subsequent optical measurement signal from a different catheter optical port after a predetermined time of acquiring the optical measurement signal.

27. The non-transitory computer-readable medium of claim 26, wherein the operations further comprise:

assigning a subsequent input time stamp to the subsequent optical measurement signal when the subsequent optical measurement signal is first acquired from the different catheter optical port and a subsequent switching time stamp to the subsequent optical measurement signal when the subsequent optical measurement signal is no longer being acquired from the different catheter optical port, wherein the subsequent input time stamp and the subsequent switching time stamp are also used when synchronizing.

28. The non-transitory computer-readable medium of claim 26, wherein the processing further comprises:

processing the optical measurement signal and the subsequent optical measurement signal in order to acquire a denaturation result, wherein the denaturation result is also used when synchronizing.

29. The non-transitory computer-readable medium of claim 26, wherein the operations further comprise:

switching an input of a processor from the catheter optical port to the different catheter optical port after the predetermined time.

30. The non-transitory computer-readable medium of claim 26, wherein the predetermined time is 2 milliseconds.

31. The non-transitory computer-readable medium of claim 26, wherein the predetermined time is 1 millisecond.

32. The non-transitory computer-readable medium of claim 23, wherein the processing further comprises:

calculating birefringence, polarization, phase retardation, or another optical property of a tissue from the optical measurement signal in order to acquire the denaturation result.

33. The non-transitory computer-readable medium of claim 23, wherein the operations further comprise:

displaying the estimated lesion depth on a user interface.

* * * * *